(12) United States Patent
Dourdeville et al.

(10) Patent No.: US 10,001,463 B2
(45) Date of Patent: Jun. 19, 2018

(54) DISPENSING NEEDLE FOR A FRACTION COLLECTOR

(71) Applicant: Waters Technologies Corporation, Milford, MA (US)

(72) Inventors: Theodore A. Dourdeville, Falmouth, MA (US); Joshua A. Burnett, Taunton, MA (US); James E. Usowicz, Webster, MA (US); Marc E. Lemelin, Douglas, MA (US); Lucas O. Tiziani, Seekonk, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 0 days. days.

(21) Appl. No.: 15/690,614

(22) Filed: Aug. 30, 2017

(65) Prior Publication Data

US 2017/0363590 A1    Dec. 21, 2017

Related U.S. Application Data

(62) Division of application No. 14/632,073, filed on Feb. 26, 2015, now Pat. No. 9,791,423.

(Continued)

(51) Int. Cl.
  *G01N 30/80*  (2006.01)
  *B01L 3/02*   (2006.01)
  *G01N 30/02*  (2006.01)
(52) U.S. Cl.
  CPC ............ *G01N 30/80* (2013.01); *B01L 3/0241* (2013.01); *B01L 2300/0838* (2013.01); *B01L 2300/165* (2013.01); *G01N 2030/027* (2013.01)

(58) Field of Classification Search
  CPC .............. G01N 30/80; G01N 2030/027; B01L 3/0241; B01L 2300/0838; B01L 2300/165
  See application file for complete search history.

(56) References Cited

U.S. PATENT DOCUMENTS 6,694,265 B2  2/2004  Gorenstein
7,337,654 B2  3/2008  Tomita et al.
(Continued)

FOREIGN PATENT DOCUMENTS

EP    1795264 A1    6/2007

OTHER PUBLICATIONS

Examination Report in UK Patent Application No. GB1502563.8, dated Jan. 19, 2017; 4 pages.

(Continued)

*Primary Examiner* — Lisa Caputo
*Assistant Examiner* — David Z Huang
(74) *Attorney, Agent, or Firm* — Schmeiser, Olsen & Watts LLP; William G. Guerin

(57) ABSTRACT

Described is a dispensing needle for a fraction collector. The dispensing needle includes a conduit having a fluid channel to conduct a chromatographic flow, an interior wall that defines the fluid channel, an exterior surface and an endface through which the chromatographic flow is dispensed. The dispensing needle also includes a coating of a hydrocarbon material or a fluorocarbon material that is bonded to the endface. The coating is also bonded to at least a portion of the exterior surface that is adjacent to the endface and at least a portion of the interior wall that is adjacent to the endface. The coating operates to reduce a droplet volume of a liquid dispensed from the endface that may remain at the tip of the dispensing needle. Consequently, the concentration variation in a collected fraction due to a missing droplet or extra droplet is reduced.

11 Claims, 8 Drawing Sheets

Related U.S. Application Data

(60) Provisional application No. 61/946,202, filed on Feb. 28, 2014, provisional application No. 62/086,320, filed on Dec. 2, 2014.

(56) References Cited

U.S. PATENT DOCUMENTS

| | | |
|---|---|---|
| 7,985,188 B2 | 7/2011 | Felts et al. |
| 2002/0102185 A1 | 1/2002 | Tatsumi |
| 2005/0006291 A1 | 1/2005 | Iwata |

OTHER PUBLICATIONS

"Molecular Vapour Deposition," Scotech Ltd., Nov. 12, 2012; 2 pages.
Combined Search and Examination Report in UK Application No. GB1502563.8, dated Oct. 8, 2015; 9 pg.
Agilent Technologies, "Agilent 1260 Infinity Analytical-scale Fraction Collector: Features, Technical Details, Specifications and Ordering Details", Jul. 1, 2010, Agilent.com; 4 pages.
Agilent Technologies, "Agilent 1260 Infinity Analytical-scale and Preparative-scale Fraction Collectors: User Manual", 2010, Agilent.com; 162 pages.
Thermo Fisher Scientific, "Thermo Scientific Dionex AFC-3000 Automated Fraction Collector", 2013, ThermoScientific.com; 3 pages.
Thermo Fisher Scientific, "Thermo Scientific Dionex UltiMate 3000 Series: Automated Fraction Collector AFC-3000 Operating Instructions", Oct. 2013, Revision 1.2, ThermoScientific.com, 88 pages.
Agilent Technologies, "Agilent 1200 Series Purification Systems", Aug. 1, 2009, Agilent.com; 12 pages.
Examination Report in UK Patent Application No. 1502563.8, dated Mar. 31, 2016; 6 pages.
Non-Final Office Action in U.S. Appl. No. 14/632,073, dated Dec. 28, 2016; 12 pages.
Final Office Action in U.S. Appl. No. 14/632,073, dated Apr. 20, 2017; 11 pages.
Notice of Allowance in U.S. Appl. No. 14/632,073, dated Jun. 28, 2017; 10 pages.
Examination Report in UK Patent Application No. GB1502563.8, dated Feb. 26, 2018; 3 pages.

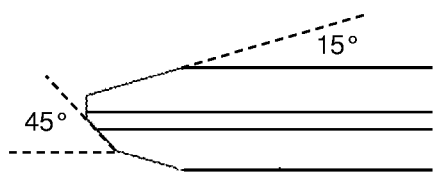
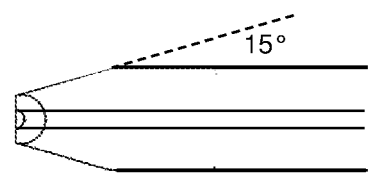
*FIG. 6A*  *FIG. 6B*
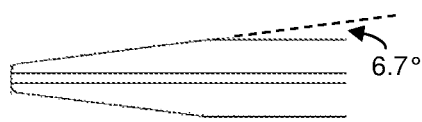
*FIG. 7*
*FIG. 8*

DISPENSING NEEDLE FOR A FRACTION COLLECTOR

RELATED APPLICATIONS

This application is a divisional of U.S. patent application Ser. No. 14/632,073, filed on Feb. 26, 2015, which claims the benefit of the earlier filing dates of U.S. Provisional Patent Application Ser. No. 61/946,202, filed Feb. 28, 2014 and titled "Fraction Collector for a Liquid Chromatography System," and U.S. Provisional Patent Application Ser. No. 62/086,320, filed Dec. 2, 2014 and titled "Dispensing Needle for a Fraction Collector," the entireties of which are incorporated herein by reference.

FIELD OF THE INVENTION

The invention relates generally to a fraction collector for a liquid chromatography system. More particularly, the invention relates to a dispensing needle for a fraction collector which can more accurately dispense fractions.

BACKGROUND

A fraction collector typically refers to an apparatus that is positioned in the outlet flow stream of a liquid chromatography system and used to collect portions of the system flow into separate collection vessels such as sample tubes or vials. Each collected portion is referred to as a fraction. Each fraction is obtained by collecting the entire liquid chromatography system flow starting at a specific time and continuing for a time window of fixed duration. Alternatively, the collection of each fraction may be initiated at the start of detection of a corresponding compound in the liquid chromatography system flow. In general, the collection of each fraction starts at a different time and the durations of the collected fractions are typically different.

A conventional hardware configuration for a fraction collector includes a diverter valve that, in one state, directs the liquid chromatography system flow to a waste channel and, in a second state, directs the liquid chromatography system flow to a collection tube or dispensing needle. As used herein, "collection tube" and "dispensing needle" are used synonymously and refer to a structure having a fluid channel through which a liquid flows from the diverter valve to a collection vessel. The dispensing needle generally is in the form of a flexible tube or other conduit that extends from the diverter valve and terminates at the other end as a dispensing needle tip which dispenses liquid into the collection vessel.

Typically, multiple collection vessels are available and the collection of a particular fraction is preceded by automated movement of the collection tube so that the dispensing needle is positioned at the opening of a corresponding collection vessel. To begin collecting a fraction, the diverter valve is actuated so that the system flow of the liquid chromatography system is diverted through the dispensing needle to the appropriate collection vessel instead of passing through the waste channel. The size of droplets dispensed from the needle tip impacts the repeatability and accuracy of the volumes of the collected fractions. In addition, analyte concentration typically changes throughout the duration of a fraction collection event. Consequently, poor volume repeatability attributable to droplet volume negatively affects fraction concentration repeatability.

SUMMARY

In one aspect, a dispensing needle for a fraction collector includes a conduit having a fluid channel to conduct a chromatographic flow, an interior wall defining the fluid channel, an exterior surface and an endface through which the chromatographic flow is dispensed. The dispensing needle also includes a coating of a hydrocarbon material covalently bonded to the endface, to at least a portion of the exterior surface and to at least a portion of the interior wall. The portions of the exterior surface and the interior wall are adjacent to the endface. The coating of hydrocarbon material operates to reduce a droplet volume of a liquid dispensed from the endface of the needle tip.

In another aspect, a dispensing needle for a fraction collector includes a conduit having a fluid channel to conduct a chromatographic flow, an interior wall defining the fluid channel, an exterior surface and an endface through which the chromatographic flow is dispensed. The dispensing needle also includes a coating of a fluorocarbon material covalently bonded to the endface, to at least a portion of the exterior surface and to at least a portion of the interior wall. The portions of the exterior surface and the interior wall are adjacent to the endface. The coating of fluorocarbon material operates to reduce a droplet volume of a liquid dispensed from the endface of the needle tip.

BRIEF DESCRIPTION OF THE DRAWINGS

The above and further advantages of this invention may be better understood by referring to the following description in conjunction with the accompanying drawings, in which like reference numerals indicate like elements and features in the various figures. For clarity, not every element may be labeled in every figure. The drawings are not necessarily to scale, emphasis instead being placed upon illustrating the principles of the invention.

FIG. 6A shows a needle tip of a dispensing needle that was evaluated to determine the volume of dispensed droplets and FIG. 6B shows the needle tip of FIG. 6A rotated 90° about its longitudinal axis.

FIG. 7 shows a needle tip for another dispensing needle that was evaluated to determine the volume of dispensed droplets.

FIG. 8 shows a needle tip for another dispensing needle that was evaluated to determine the volume of dispensed droplets.

DETAILED DESCRIPTION

Reference in the specification to "one embodiment" or "an embodiment" means that a particular, feature, structure or characteristic described in connection with the embodiment is included in at least one embodiment of the teaching. References to a particular embodiment within the specification do not necessarily all refer to the same embodiment.

In brief overview, the invention relates to a dispensing needle for a fraction collector. The dispensing needle includes a conduit having a fluid channel to conduct a chromatographic flow, an interior wall that defines the fluid channel, an exterior surface and an endface through which the chromatographic flow is dispensed. The dispensing needle also includes a coating of a hydrocarbon material or a fluorocarbon material that is bonded to the endface. The coating is also bonded to at least a portion of the exterior surface that is adjacent to the endface and at least a portion of the interior wall that is adjacent to the endface. The coating operates to reduce a droplet volume of a liquid dispensed from the endface.

The present teaching will now be described in more detail with reference to embodiments thereof as shown in the accompanying drawings. While the present teaching is described in conjunction with various embodiments and examples, it is not intended that the present teaching be limited to such embodiments. On the contrary, the present teaching encompasses various alternatives, modifications and equivalents, as will be appreciated by those of skill in the art. Those of ordinary skill having access to the teaching herein will recognize additional implementations, modifications and embodiments, as well as other fields of use, which are within the scope of the present disclosure as described herein.

Figure 1:
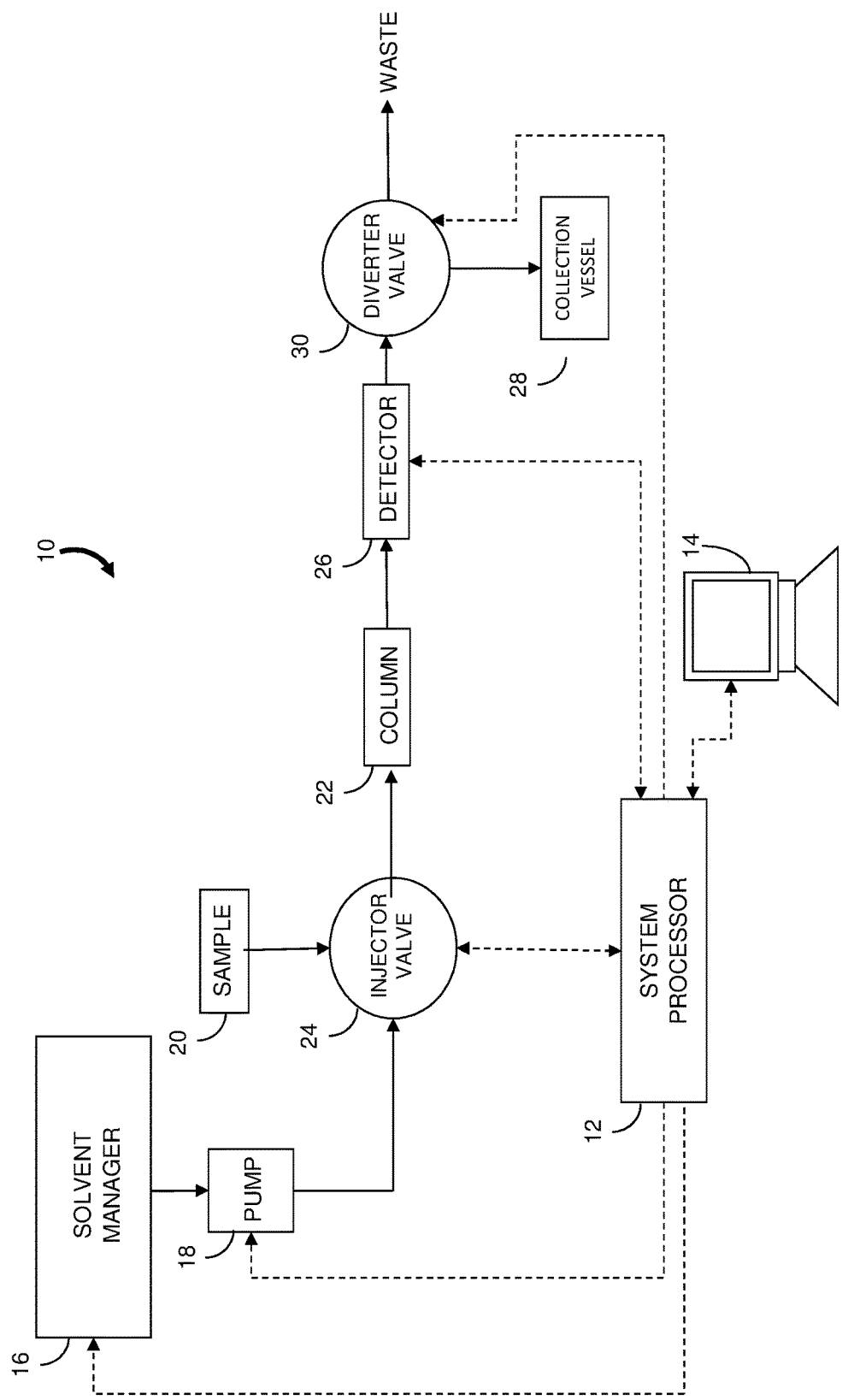
FIG. 1 is a block diagram of a liquid chromatography system that can be used to practice embodiments of the method of the invention.

FIG. 1 is a block diagram of a liquid chromatography system 10 that can be used with embodiments of the invention. The system 10 includes a system processor 12 (e.g., microprocessor and controller) in communication with a user interface device 14 for receiving input parameters and displaying system information to an operator. The system processor 12 communicates with a solvent manager 16 which provides one or more solvents for a mobile phase. A pump system 18 includes one or more pump heads that may be configured in a variety of ways. A sample from a sample reservoir, or sample container, 20 is injected into the mobile phase upstream from a chromatographic column 22 through an injector valve 24. The chromatographic column 22 is coupled to a detector 26 which provides a signal to the system processor 12 that is responsive to various components detected in the eluent from the column 22.

Figure 2:
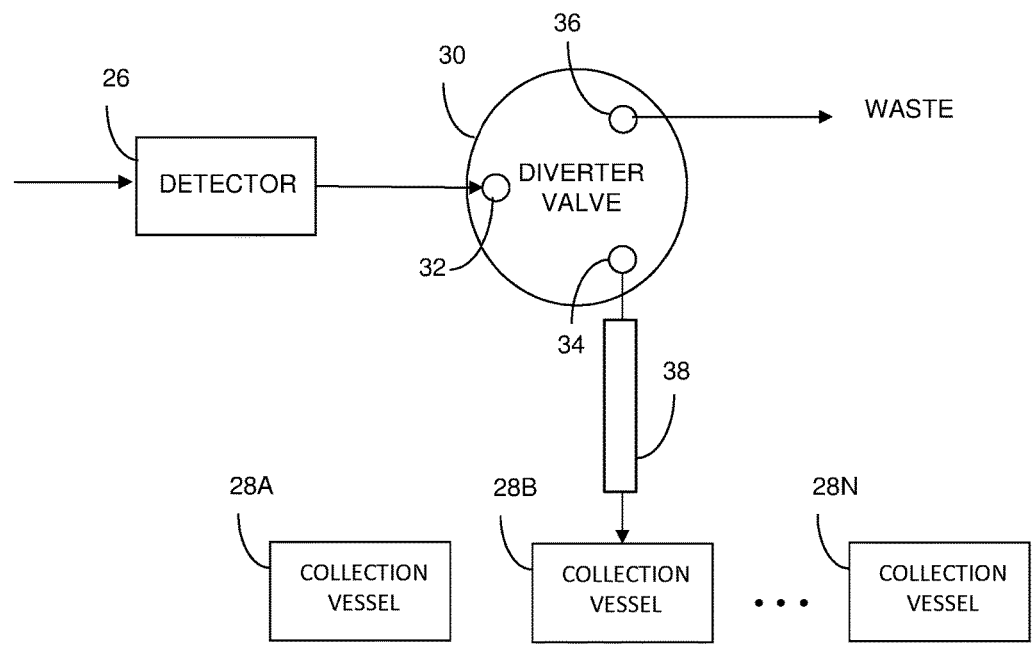
FIG. 2 is a functional block diagram of a portion of a conventional fraction collector for a liquid chromatography system.

After passing through the detector 26, the system flow exits to a waste port; however, when collecting a fraction, the system flow is diverted to a collection vessel 28. Examples of collection vessels includes vials, sample tubes, the wells in microtiter plates and microwell plates, as well as Matrix Assisted Laser Desorption Ionization (MALDI) plates and similar two-dimensional substrates on which collected fractions may be deposited. As shown in the block diagram of FIG. 2, the diversion of the system flow is achieved by actuating a diverter valve 30 so that the system flow at an inlet port 32 is redirected to a collection port 34 instead of a waste port 36. The system flow from the collection port 34 flows through a dispensing needle (i.e., collection tube) 38 that typically is controlled for motion so that different fractions collected during a single separation can be directed from a dispensing end of the dispensing needle 38 to one of a number N of collection vessels 28. The dispensing needle 38 has a needle tip at the dispensing end which, in some instances, may be geometrically and otherwise different from the remainder of the dispensing needle 38. Typically, the dispensing needle 38 is flexible along most or all of its length such that the needle tip can be positioned near or at an opening of the appropriate collection vessel 28 prior to the start of the collection window for the respective fraction.

Figure 3:
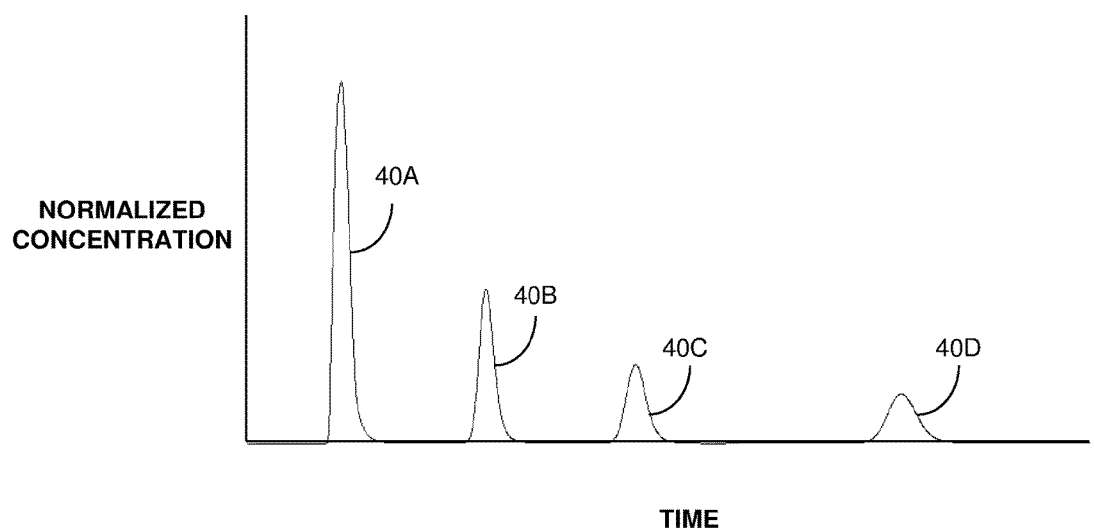
FIG. 3 is a chromatogram showing four fractions to be collected at different times.

By way of an example, FIG. 3 graphically depicts a chromatographic separation having four fractions 40A to 40D to be collected at different times. Each fraction 40 corresponds to a different compound in the system flow and is collected in a separate collection vessel after moving the tip of the dispensing needle to the corresponding collection vessel.

The size of the droplets dispensed from the needle tip affects the accuracy and repeatability of the volumes of the collected fractions. The concentration of an analyte typically changes throughout the duration of a fraction collection event, therefore poor volume repeatability adversely affects fraction concentration repeatability and results in larger relative standard deviations (RSDs) for re-injected fractions.

Ideally, the number of droplets dispensed into a collection vessel is the same for each fraction collection of an analyte; however, for some collections a number N of droplets are collected, while in other collections the number of droplets collected differs by one so that N−1 or N+1 droplets are collected. If the volume of a single droplet is a significant portion of the total collection volume for the fraction, a variation of one droplet will have a significant impact on the concentration RSD.

To address the above problem, embodiments of a dispensing needle for a fraction collector as described below yield a smaller droplet volume. Consequently, the concentration variation associated with missing or extra droplets is reduced. As the volume of each droplet is reduced to approach zero, the dispensed liquid transitions from a sequence of droplets to a stream. Thus the same effects that reduce the size of the droplets also influence the transition point between droplets and a steady stream. Various embodiments described herein allow for low flow rates while maintaining an acceptable pressure drop through the dispensing needle. Some embodiments described below include a conduit in which the cross-sectional area of the fluid channel in a needle tip at the end of the conduit is smaller than the cross-sectional area of a fluid channel in the conduit. The result is an increase the velocity of the liquid dispensed from the needle tip relative to the velocity of the liquid in the conduit. Other embodiments of a dispensing needle include a coating that reduces adherence of liquid at the needle tip to thereby reduce the volume of any droplets that remain on the exterior surface of the needle tip.

Figure 4:
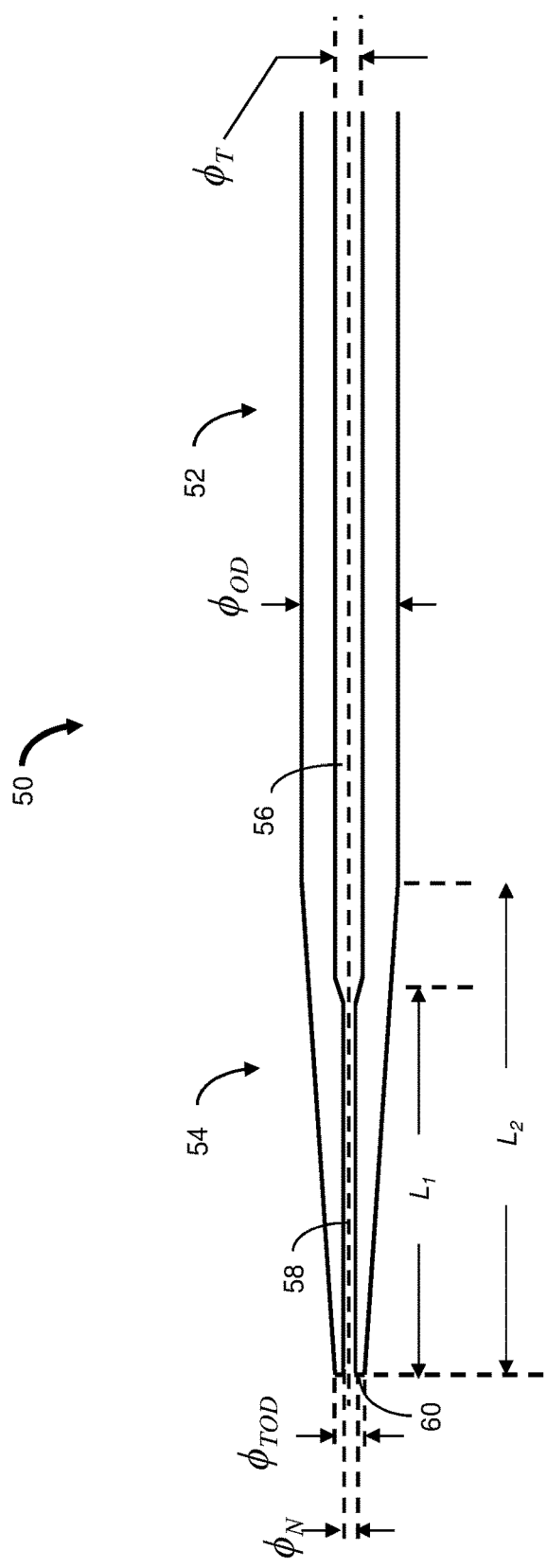
FIG. 4 is an illustration of an embodiment of a dispensing needle for a fraction collector.

FIG. 4 is an illustration of an embodiment of a dispensing needle 50 for a fraction collector. Only a portion of the length of the needle 50 is shown as the full length is approximately 48 cm (approximately 19 in.). The dispensing needle 50 is in the form of a conduit 52 with a needle tip 54 defined at the dispensing end. For example, the conduit 52 can be a flexible cylindrical metal tubing. The other end (not shown) of the dispensing needle 50 is configured for coupling to a diverter valve (e.g., the diverter valve 30 in FIG. 2). As illustrated, the conduit 52 and needle tip 54 are formed as a single integral body. In an alternative embodiment, the needle tip 54 is fabricated as a separate piece and then attached, for example, by a welding process, to the conduit 52. In one embodiment, the conduit 52 and the needle tip 54 are formed from MP35N® alloy which is a bio-compatible nonmagnetic nickel-cobalt-chromium-molybdenum alloy. In other embodiments, the conduit 52 and the needle tip 54 are formed of other materials such as polyether ether ketone (PEEK), fused silica or other glass, ceramic, stainless steel, titanium or titanium alloy, or other metal.

The conduit 52 has an interior wall that defines an axial fluid channel 56 of diameter $\phi_T$ over most or all of its length. The needle tip 54 has an axial fluid channel 58 having a diameter $\phi_N$ over a length $L_1$. The conduit fluid channel diameter $\phi_T$ is greater than the fluid channel diameter $\phi_N$ at the needle tip 54 and the length of the transition between the two diameters $\phi_N$ and $\phi_T$ occurs over a non-zero distance, for example, over 10 mm (0.40 inch) or less. The outer surface of the dispensing needle 50 has a constant diameter $\phi_{OD}$ along its length except for a short distance $L_2$ referenced from the endface 60 of the needle tip 54. The outer surface of the needle tip 54 has a truncated conical shape over the length $L_2$ along which the outer surface diameter tapers down to a minimum value $\phi_{TOD}$ at the endface 60.

Various methods can be employed to fabricate the dispensing needle 50. For example, a swaging process can be applied to a piece of flexible metal tubing of inner diameter $\phi_T$. In this process, an end portion of the tubing is compressed, or squeezed, evenly around the circumference to permanently deform the tubing and to produce the smaller diameter $\phi_N$ and cross-sectional area of the fluid channel 58 in the needle tip 54. The length of the tubing may increase slightly as a result of the swaging process. After completing the swaging process, a grinding operation is performed to achieve the desired truncated conical shape for the outer surface of the needle tip 54. Generally, the amount of tubing material removed in the grinding process decreases with distance from the endface 60. As an alternative to the grinding operation, a metal etching process such as electroetching can be used to obtain the desired shape of the outer surface. Advantages of electroetching, or elecrosharpening, include the capability to produce finer needle tips than shaping by mechanical methods, such as grinding, where machining marks and burs on the surface may occur.

Advantageously, the smaller cross-sectional area of the fluid channel 58 in the needle tip 54 results in an increase in the linear velocity of liquid dispensed from the endface 60 and a reduction in the volume of any droplets that may form at the endface 60 and adjacent portion of the truncated conical surface. Depending on the particular cross-sectional areas of the fluid channels 56 and 58, and the flow rate and composition of the liquid, droplets may be prevented from forming at the endface 60. The limited axial length $L_1$ of the smaller fluid channel 58 results in a lower fluid pressure increase that would otherwise be possible for a longer length, such as by simply using the smaller diameter $\phi_N$ for the full length of the dispensing needle 50. Advantageously, the small increase in fluid pressure realized using the illustrated embodiment is acceptable according to pressure limitations of typical diverter valves which may be of the order of 1.7 MPa (i.e., a few hundred PSI).

By way of a specific and non-limiting numerical embodiment, the outer diameter $\phi_{OD}$ and the inner diameter $\phi_T$ of the conduit 52 are 0.63 mm (0.025 in.) and 0.18 mm (0.007 in.), respectively, and the inner diameter $\phi_N$ of the needle tip 54 is 0.08 mm (0.003 in.). The inner diameter $\phi_N$ of the needle tip 54 extends axially for a length $L_1$ of approximately 2.3 mm (0.090 in.). The exterior surface of the needle tip 54 has a cone angle of approximately 4.7° and, over an axial length $L_2$ of approximately 2.8 mm (0.110 in.), tapers down to a diameter $\phi_{TOD}$ of 0.18 mm (0.007 in.) at the endface 60. In this example, a smaller value of the cross-sectional area of the fluid channel 58 in the needle tip 54 results in a dispensed liquid velocity that is approximately 5.4 times the liquid velocity in the larger fluid channel 56. In addition, the small area of the endface 60 represents a reduced surface area to which a droplet may cling.

The cross-sectional areas need not be circular. For example, the cross-sections of the fluid channels may be rectangular or have other shapes. In addition, the cross-sectional areas are not required to be constant along the axial lengths of the fluid channels, as long as the average of the cross-sectional area of the fluid channel in the needle tip is less than the average of the cross-sectional area of the fluid channel in the conduit.

Hydrophobic Needle Coating

Certain embodiments of a dispensing needle include a coating that reduces the adherence of liquid to the exterior surface of the needle tip, including the endface. The coating may be a single layer of coating material or may be a combination of two or more coating layers of different coating materials. Thus the volume of liquid and any associated compound from the collected fraction that remains on the exterior of the dispensing needle in an uncollected droplet is reduced. Reducing the probability and volume of an adhering droplet results in a reduction in cross-contamination of the next collected fraction. Some of the compounds that are collected may have a natural affinity for the material of the dispensing needle. The coating can effectively reduce the affinity of these compounds. Instead of adhering to the outer surface, any droplets that do form are repelled by the coating and are therefore more likely to fall from the needle tip into the collection vessel.

Figure 5:
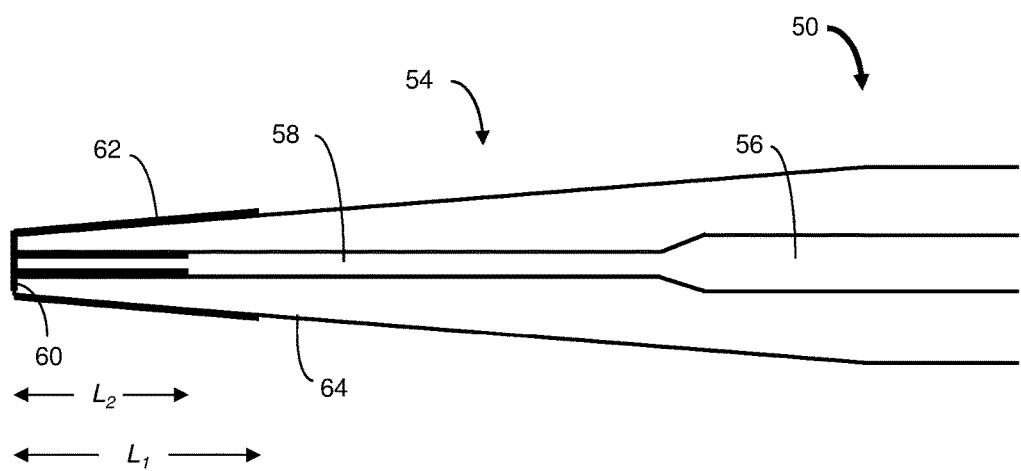
FIG. 5 is an expanded view of the dispensing needle shown in FIG. 4 and depicts a coating used to repel a droplet.

To properly function to control the droplet size at the needle tip, the coating should be on the endface, at least a portion of the interior wall surrounding the fluid channel that is adjacent to the endface, and on at least a portion of the exterior surface of the needle tip that is adjacent to, or "abutting," the endface. As an example and with reference to FIG. 5 which is an expanded view of the embodiment of a dispensing needle 50 shown in FIG. 4, a coating (depicted as bolded line 62) to repel a droplet is deposited on the endface 60, on a portion of the conical exterior surface 64 of the needle tip 54 extending for a length $L_1$ from to the endface 60, and along the interior wall of the fluid channel 58 for a short length (e.g., $L_2$) from the endface 58. Coating deposition can be limited to selected external surface areas by masking external surfaces that are not to be coated prior to performing the coating process. The axial length of the coating 62 that resides on the wall of the fluid channel 58 is in practice much longer than illustrated as masking of the fluid channels 56, 58 is generally not possible, and in some embodiments the entire lengths of the interior walls of the fluid channels 56, 58 may be coated. In alternative embodiments, no masking is used during the deposition process and most or all of the exterior surfaces of the conduit 52 and needle tip 54 are coated.

In some embodiments the coating includes at least one layer of a hydrophobic material so that polar solvents will be repelled. The hydrophobic coating material can be a hydrocarbon or a fluorocarbon that covalently bonds to the surface of the dispensing needle and which modifies the surface wettability characteristic.

In one embodiment, the surface of the dispensing needle is passivated by applying a single layer of diamond-like carbon (DLC) which may be deposited, for example, using a chemical vapor deposition (CVD) process. By way of a non-limiting example, the thickness of a DLC coating may be less than one μm to more than 10 μm. In an alternative embodiment, the dispensing needle is passivated with a bi-layer of different hydrophobic materials that are selected not only to repel polar solvents but also to decrease the adherence of organic solvents. The first applied layer, or lower layer, is deposited on the external needle surface and is used to promote adhesion of the second applied layer, or upper layer. The thickness of the first deposited (lower) layer may be chosen to mask the surface properties of the needle from the second deposited (upper) layer which is more hydrophobic. The second layer is preferably thinner than the first layer and may be only a few molecules thick.

In a preferred process, the coating is applied using a Molecular Vapor Deposition (MVD®) coating tool such as coating system model no. MVD100E available from Applied Microstructures, Inc. of San Jose, Calif. The MVD process enables an organic molecular layer of material to be covalently bonded to the surface of the dispensing needle. The deposited coating may be a self-assembled monolayer (SAM). The SAM can be based on molecules having a sufficiently long carbon chain length (e.g., C6 or greater) to mask the surface in terms of the ability of the surface to react with analytes in the liquid flowing through and dispensed from the needle. At the same time, the carbon chain length of the SAM should be less than the carbon chain length of the surface of the stationary phase in the chromatographic column to ensure that a solvent sufficient to release the analyte from the chromatography column will prevent retention of the analyte as it passes through and is dispensed from the needle. Various concerns such as precursor stability can determine the preferred linkage chemistry (e.g., monopodal or bipodal attachment) that is used as long as the SAM orientation of the overall molecular backbone is achieved. In one embodiment, the SAM is formed as a hydrocarbon having a C10 chain length.

Dispensing Needle Evaluation

A series of tests were performed to determine the size of droplets that are formed and dispensed from various configurations of dispensing needles. The measurements were made to evaluate the influence of various parameters on droplet volume, including solvent composition, flow rate, needle tip geometry and needle coatings. The flow path for the tests was defined by an Acquity® Binary Solvent Manager (BSM) (available from Waters Corporation of Milford, Mass.) that was coupled to a 2.1 mm×50 mm chromatographic column acting as a flow restrictor which in turn was coupled to the dispensing needle under evaluation. The flow rates used for testing ranged from 0.1 mL/min to 1.0 mL/min in 0.1 mL/min increments. Solvent compositions for the mobile phase used in the testing ranged from 0% to 100% acetonitrile (ACN) in water in 10% increments.

Table 1 lists the nine different dispensing needles that were evaluated and the corresponding needle tip inner diameter (ID) in inches, tip taper angle measured from the needle tip axis and the surface coating for each dispensing needle. For reference herein, each dispensing needle is identified below by a corresponding reference (letters A to I).

The first-listed dispensing needle A is formed of stainless steel and has an inner diameter of 0.010 in. Unlike the other dispensing needles, the tip of dispensing needle A is not tapered or cone-shaped. The material for dispensing needle B is a polyether ether ketone (PEEK). FIG. 6A shows that the needle tip includes a 15° taper and a 45° bevel. FIG. 6B shows the needle tip of FIG. 6A rotated 90° about its longitudinal axis.

The other dispensing needles C to I are made of MP35N® alloy which is a bio-compatible nonmagnetic nickel-cobalt-chromium-molybdenum alloy. FIG. 7 shows the needle tip for dispensing needles C and D, and FIG. 8 shows the needle tip for dispensing needles E, F and G. The needle tips of dispensing needles H and I can be seen by referring again to FIG. 4.

TABLE 1

| | DISPENSING NEEDLE DESCRIPTION | TIP ID (in.) | TIP TAPER ANGLE | COATING |
|---|---|---|---|---|
| A | WFCIII tube, 0.010" ID | 0.010 | none | none |
| B | I-Class 10 μL PEEK needle | 0.007 | 15° (45° bevel) | none |
| C | Bio-FTN 15 μL MP35N needle | 0.005 | 6.7° | none |
| D | FTN 15 μL SS needle with DLC coating | 0.005 | 6.7° | DLC |
| E | MP35N FMA needle, short taper | 0.007 | 9.0° | none |
| F | MP35N FMA needle, short taper with B1 coating | 0.007 | 9.0° | B1 |
| G | MP35N FMA needle, short taper with B1/B7 coating | 0.007 | 9.0° | B1/B7 |
| H | Swaged-tip MP35N FMA | 0.003 | 4.7° | none |
| I | Swaged-tip MP35N FMA with B1/B7 coating | 0.003 | 4.7° | B1/B7 |

Figure 9:
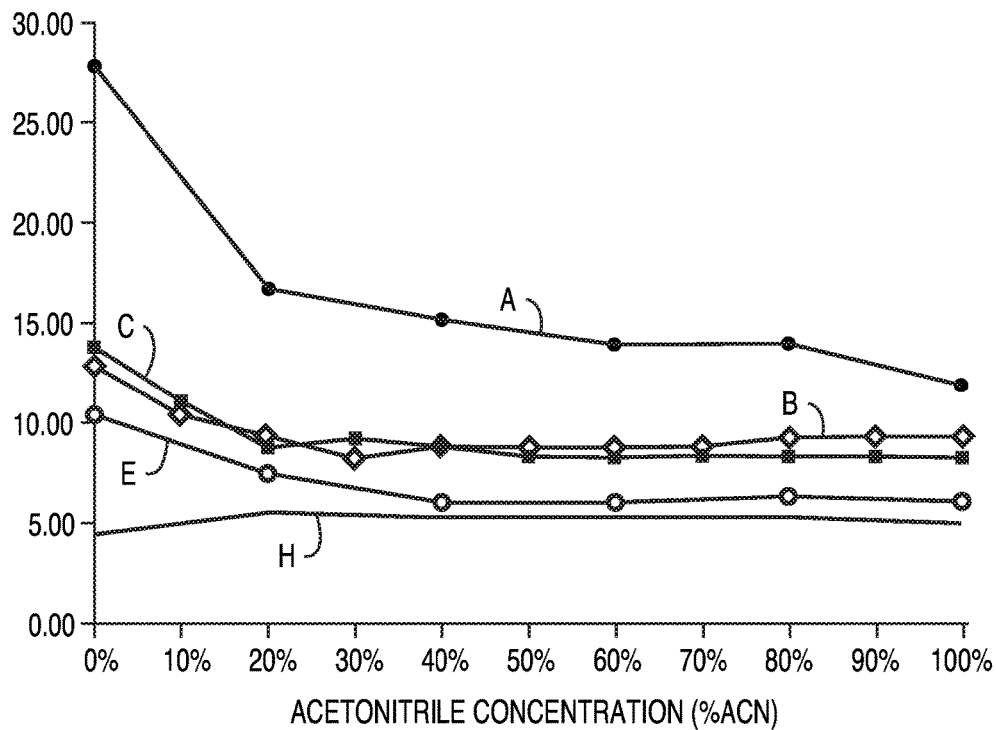
FIG. 9 is a graphical representation of the relationship between droplet volume and solvent composition for certain uncoated dispensing needles.

FIG. 9 graphically depicts the relationship between droplet volume and solvent composition for the uncoated dispensing needles A, B, C, E and H listed in Table 1. Acetonitrile concentration has an observable effect on the droplet volume. The effect is most pronounced at lower concentrations of acetonitrile. The swaged-tip needle (H) does not exhibit much sensitivity to the concentration of acetonitrile. The flow rate of the solvent was 0.5 mL/min except for the swaged-tip needle which was tested at a flow rate of 0.3 mL/min. At a flow rate of 0.5 mL/min (at 50% acetonitrile), the swaged-tip needle did not dispense droplets but instead dispensed a stream of solvent.

Figure 10:
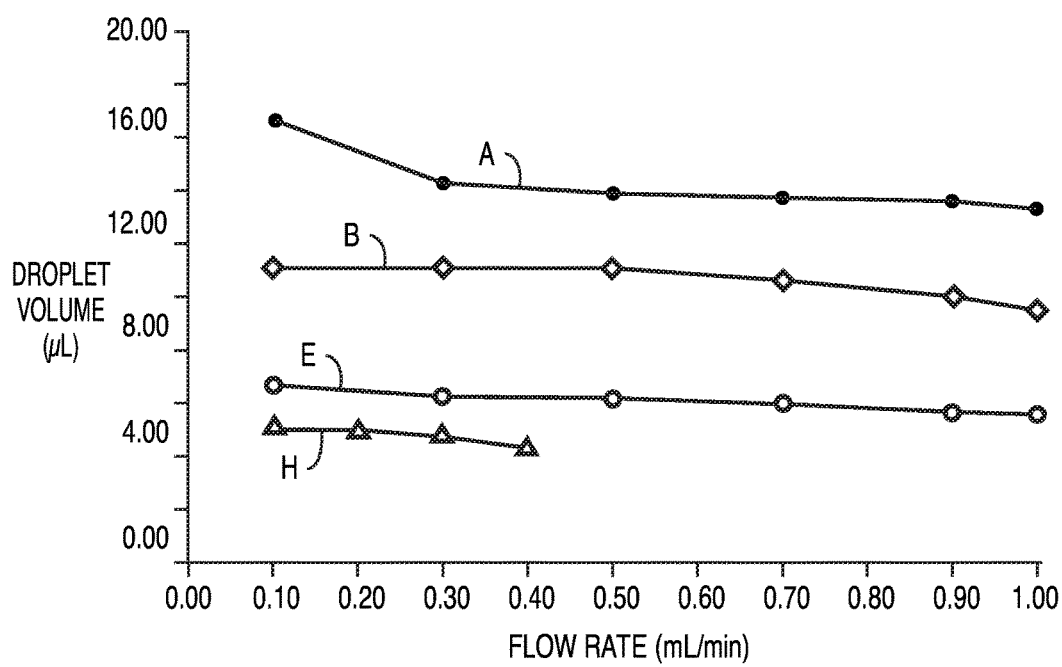
FIG. 10 is a graphical representation of the droplet volume determined as a function of flow rate for four different uncoated dispensing needles.

FIG. 10 is a graphical representation of the droplet volume determined as a function of flow rate for four different uncoated dispensing needles A, B, E and H. All four dispensing needles exhibited a slight decrease in the droplet volume as the flow rate increases. The droplet volume for the swaged-tip needle (H) decreases with increasing flow rate and is lower than the droplet volume of any of the other three dispensing needles regardless of flow rate. At a flow rate of approximately 0.50 mL/min., the swaged-tip dispensing needle is observed to transition from droplets to a stream while the other dispensing needles were observed to dispense droplets up to the highest test flow rate of 1.0 mL/min.

Figure 11:
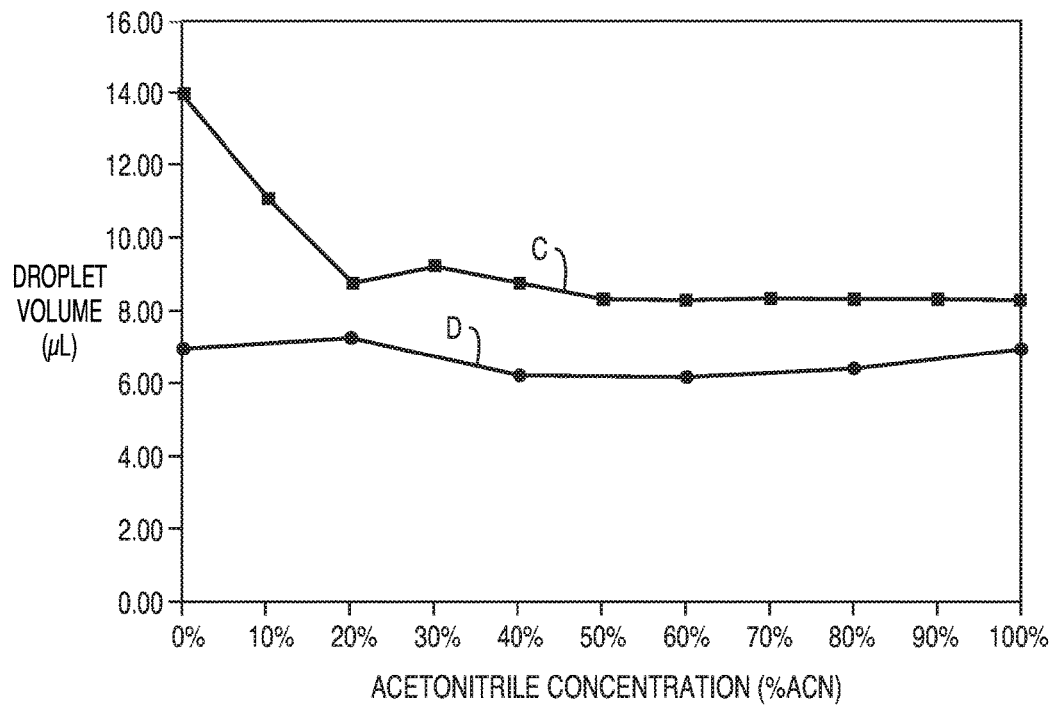
FIG. 11 is a graphical representation of the droplet volume determined as a function of acetonitrile concentration for a dispensing needle with a diamond-like coating.

The effect of a diamond-like coating (DLC) was evaluated to determine its effect on droplet volume as a function of acetonitrile concentration. The results of the evaluation for an uncoated and a coated version of the same type of dispensing needle, C and D, respectively, are shown in FIG. 11. The DLC coated dispensing needle shows a reduced droplet volume across the entire range of acetonitrile concentration, although the improvement is generally more pronounced at lower percentages of acetonitrile concentration.

Figure 12:
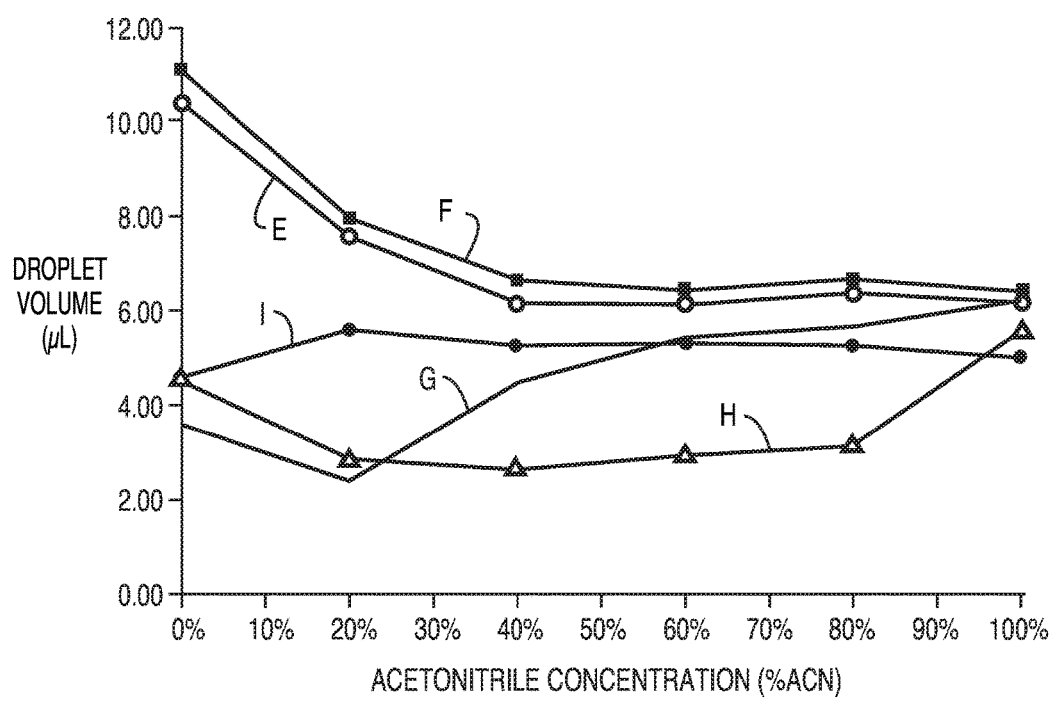
FIG. 12 is a graphical representation of the droplet volume determined as a function of acetonitrile concentration for five different dispensing needles.

FIG. 12 shows the droplet volume determined according to acetonitrile concentration for five different dispensing needles. Two of the needles E and H were uncoated, one needle F had a single layer of a moderately-hydrophobic coating B1 and two needles G and I had a two layer B1/B7 coating formed of a first deposited hydrophobic material B1 and a subsequently deposited different hydrophobic material B7.

Both the single layer B1 coating and the two layer B1/B7 coating were deposited on the inner surface of the dispensing needle (i.e., the wall of the fluid channel) and the external surfaces at a process temperature of approximately 35° C.

The droplet volumes for the swaged tip needles H and I were consistently less that the droplet volumes of the uncoated MP35N FMA needle with no coating E and with the B1 coating F across the full range of acetonitrile concentration. The MP35N needle with the dual B1/B7 coating also had a lower droplet volume than the E and F needles except at about 100% acetonitrile concentration.

Figure 13:
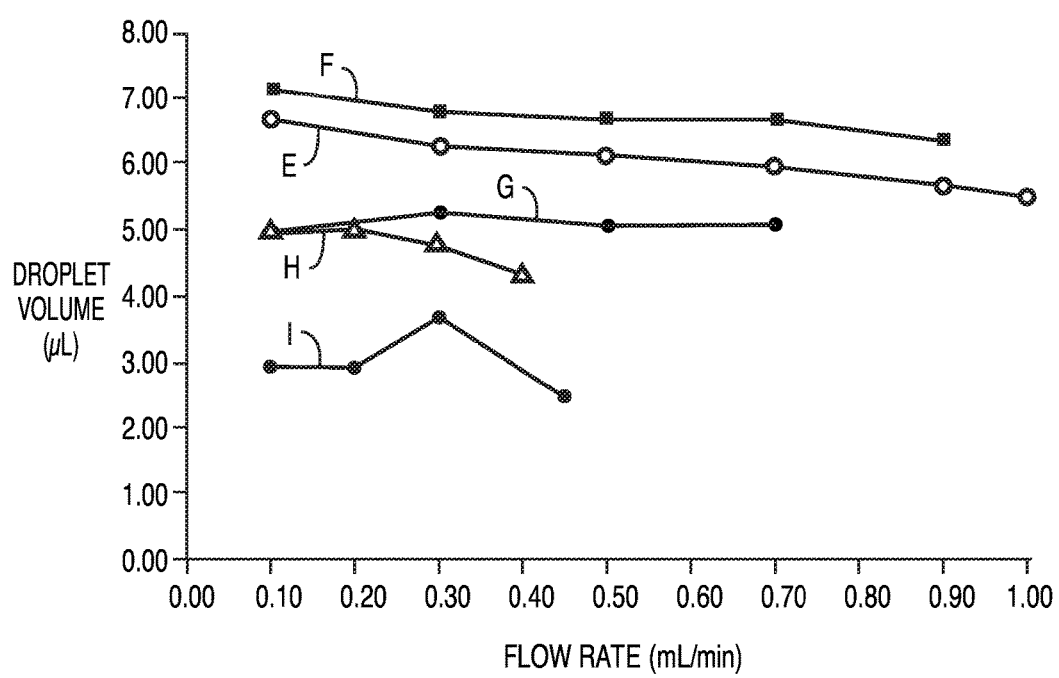
FIG. 13 is a graphical representation of the dependence of droplet volume as a function of flow rate for the dispensing needles evaluated in FIG. 12.

FIG. 13 is a graphical representation of the dependence of droplet volume as a function of flow rate for the same dispensing needles at those evaluated according to FIG. 12. The measurements were made for an acetonitrile concentration of 50%. Although the needles E and F exhibit a decrease in droplet volume with increasing flow rate, both needles are substantially above the droplet volumes of the other three needles G, H and I. The swaged tip needles do not show droplet volume for the higher flow rates as the droplets transition to a stream at a flow rate of approximately 0.5 mL/min.

From the measurement results described above and characterized by FIG. 9 to FIG. 13, it can be seen that the uncoated swaged tip dispensing needle H yielded smaller droplets that the other tested uncoated dispensing needles. Under a wide range of conditions, the droplet volume was approximately 5 µL or less. Coating the swaged-tip dispensing needle with a dual layer B1/B7 coating yielded even smaller droplet volumes which, for certain flow rates and solvent compositions, yielded droplet volumes less than 3 µL.

While the invention has been shown and described with reference to specific embodiments, it should be understood by those skilled in the art that various changes in form and detail may be made therein without departing from the spirit and scope of the invention as recited in the accompanying claims.

What is claimed is:

1. A dispensing needle for a fraction collector, comprising:
   a conduit having a first fluid channel having a first cross-sectional area and a dispensing end;
   a needle tip disposed at the dispensing end of the conduit and having an exterior surface, an interior wall defining a second fluid channel in fluid communication with the first fluid channel, and an endface disposed at a dispensing end of the second fluid channel, the second fluid channel having a second cross-sectional area that is less than the first cross-sectional area, wherein a flow rate of a liquid through the second fluid channel is greater than a flow rate of the liquid through the first fluid channel; and
   a hydrophobic coating of a fluorocarbon material covalently bonded to the endface of the needle tip, to at least a portion of the exterior surface of the needle tip adjacent to the endface and to at least a portion of the interior wall adjacent to the endface, wherein the hydrophobic coating of the fluorocarbon material operates to reduce a droplet volume of the liquid dispensed from the endface.

2. The dispensing needle of claim 1 wherein the coating of a fluorocarbon material is a self-assembled monolayer of a fluorocarbon material.

3. The dispensing needle of claim 1 wherein the coating of a fluorocarbon material is bonded by a monopodal attachment.

4. The dispensing needle of claim 1 wherein the fluorocarbon material has a carbon chain length of at least six.

5. The dispensing needle of claim 1 wherein the fluorocarbon material has a carbon chain length that is less than the carbon chain length of a stationary phase in the chromatographic flow.

6. The dispensing needle of claim 1 wherein the conduit is formed of a metal, a ceramic or a glass.

7. The dispensing needle of claim 6 wherein the conduit is formed of one of titanium, titanium alloy or fused silica.

8. The dispensing needle of claim 1 wherein the hydrophobic coating of a fluorocarbon material comprises a bi-layer comprising a first applied layer comprising a first hydrophobic material covalently bonded to the endface, at least the portion of the exterior surface and at least the portion of the interior wall, the bi-layer further comprising a second applied layer disposed on the first applied layer and comprising a second hydrophobic material that is different from the first hydrophobic material.

9. The dispensing needle of claim 8 wherein the second hydrophobic material is more hydrophobic than the first applied layer.

10. The dispensing needle of claim 1 wherein the endface is perpendicular to a longitudinal axis of the second fluid channel.

11. The dispensing needle of claim 1 wherein at least one of the first and second cross-sectional areas is a circular cross-sectional area.

* * * * *